United States Patent [19]

Furuya et al.

[11] Patent Number: 5,126,581
[45] Date of Patent: Jun. 30, 1992

[54] PARTICLE MEASUREMENT METHOD AND APPARATUS FOR DETERMINING CORRECTED PARTICLE DIAMETER

[75] Inventors: Yoshiyuki Furuya; Koichi Akiyama, both of Hino, Japan

[73] Assignee: Kowa Company Ltd., Japan

[21] Appl. No.: 593,108

[22] Filed: Oct. 5, 1990

[30] Foreign Application Priority Data

Oct. 6, 1989 [JP] Japan .................................. 1-260131

[51] Int. Cl.⁵ .......................................... G01N 15/06
[52] U.S. Cl. .................................... 250/574; 356/336
[58] Field of Search ................... 250/573, 574, 222.2; 356/335, 336, 339, 128, 338

[56] References Cited

U.S. PATENT DOCUMENTS

| | | | |
|---|---|---|---|
| 3,879,129 | 4/1975 | Inoue | 356/335 |
| 4,828,388 | 5/1989 | Namba | 356/339 |
| 4,854,705 | 8/1989 | Bachalo | 356/336 |

*Primary Examiner*—David C. Nelms
*Attorney, Agent, or Firm*—Bruce L. Adams; Van C. Wilks

[57] ABSTRACT

In a particle measurement method and apparatus, a laser beam is directed into a fluid and the intensity of light scattered by fine particles floating in the fluid is detected by a light receiving system to determine the particle diameter. A ratio of light scattering efficiency of the particles in the fluid to that in a standard fluid is determined on the base of the refractive index of the fluid in use. The particle diameter is corrected depending upon the ratio of light scattering efficiency by correcting a set value for discriminating the particle diameter or by correcting the intensity of the detected scattered light. This compensates for errors arising from the difference of the refractive index of the fluid containing the particle to be measured and assures a high accuracy in measuring the particle size.

9 Claims, 4 Drawing Sheets

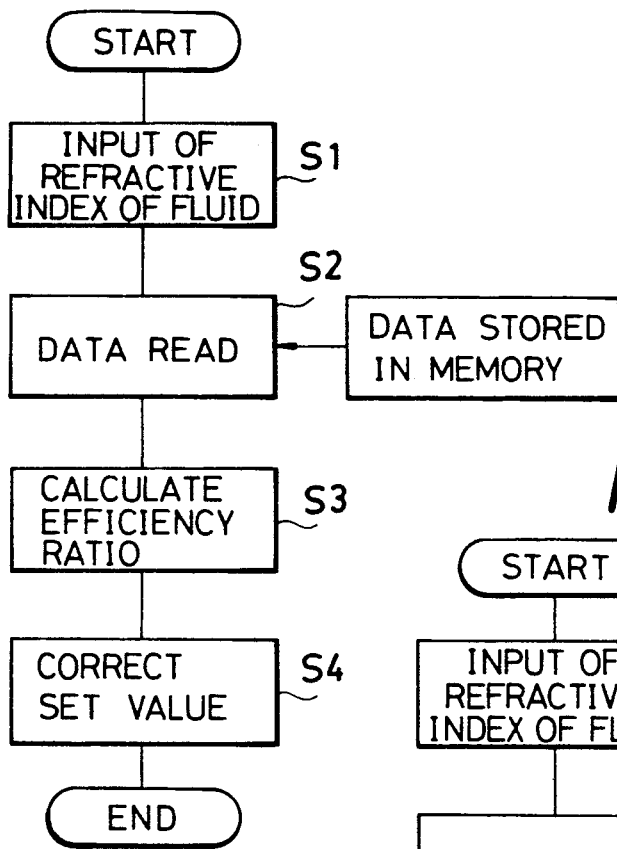
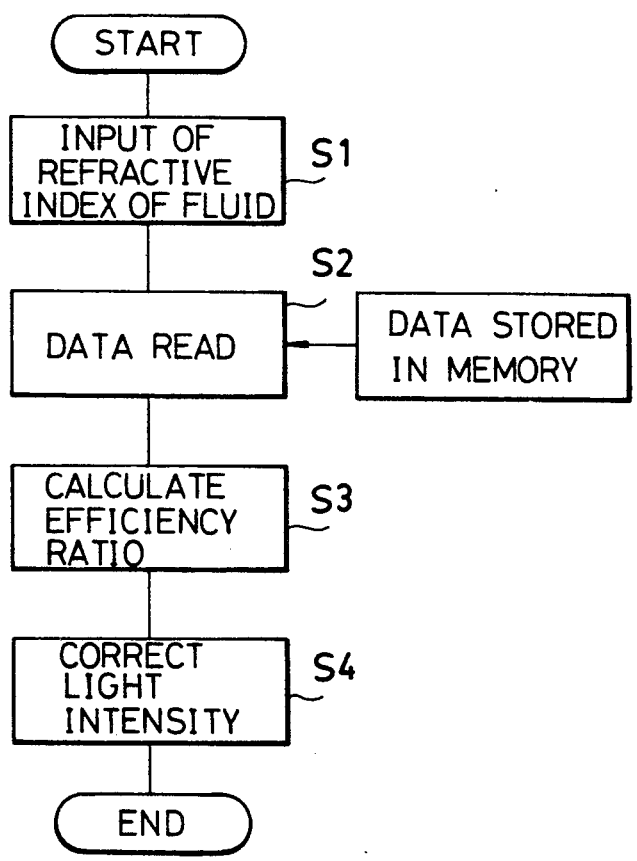

PRIOR ART

FIG. 5

| REFRACTIVE INDEX | SCATTERING EFFICIENCY RATIO |
|---|---|
| 1.30 | 1.235 |
| 1.33 | 1 |
| 1.36 | 0.787 |
| 1.39 | 0.597 |
| 1.42 | 0.432 |
| 1.45 | 0.293 |
| 1.48 | 0.181 |
| 1.51 | 0.096 |
| 1.54 | 0.038 |

PARTICLE MEASUREMENT METHOD AND APPARATUS FOR DETERMINING CORRECTED PARTICLE DIAMETER

BACKGROUND OF THE INVENTION

1. Field of the Invention

This invention relates to a method and an apparatus for measuring particles, and more particularly to a method and an apparatus for measuring the properties of particles in a fluid.

2. Description of the Prior Art

In the conventional apparatus of this type, a laser beam is directed into a fluid in a measurement cell containing the particles and the diameter of the particles is calculated from the intensity of scattered light from the particles, utilizing the fact that the intensity of the light scattered from the particles is a function of the particle diameter. Further processing is then conducted to obtain the number and density of the particles from the measured volume of the fluid.

The conventional apparatus will be explained with reference to FIG. 4. A laser beam emitted by a laser beam source 1 is converged on the measurement zone 4 within a measurement cell 3 by a lens 2. When one or more particles pass through the measurement zone, they scatter the laser light. The light scattered by the particles is condensed by a lens 5 and forms an image at a slit 6.

The light passing through the slit 6 is received by a photomultiplier 7, which converts it into an electric signal. The electric signal is amplified by a preamplifier 8 and is thereafter analyzed by an analog method or a photon-counting method using an analyzer 9 for analyzing the particle size distribution.

The relationship between the scattered light intensity and the particle diameter is generally determined experimentally using standard polystyrene latex mixed with water. However, it is known from the Mie scattering theory that the intensity of the light scattered by particles in a fluid is a function of the diameter of the particles, the refractive index of the particles and the refractive index of the fluid.

Therefore, any change in the refractive index of the fluid will modify the light scattering efficiency of the particles so that the intensity of the scattered light will differ even for one and the same particle. For concretely demonstrating this fact, the relationship between the refractive index of the fluid and the particle light scattering efficiency was investigated using a laser beam having a wavelength of 633 nm and particles having a diameter of 0.2 micrometer and a refractive index of 1.592, with the scattering efficiency at the index of refraction of 1.33 of the standard fluid (water) being defined as 1. The results are shown in FIG. 5.

Conventional apparatuses using the laser beam scattering method for measuring fine particles in a fluid are not equipped with a means capable of correcting the measured intensity of the scattered light from the particles (or the measurement conditions etc.) on the basis of the scattering efficiency, which, as shown in FIG. 5, is dependent on the refractive index of the fluid. Up to now, therefore, the fact that the intensity of the light scattered from a particle changes when the fluid (refractive index of the fluid) changes has made it impossible to conduct accurate particle diameter measurement even with respect to one and the same particle.

SUMMARY OF THE INVENTION

An object of the present invention is therefore to provide an improved particle measurement method being capable of providing precise particle measurement results.

Another object of the invention is to provide an apparatus for carrying out this method.

According to the present invention there is provided a particle measurement method and apparatus in which a laser beam is directed into a fluid, and the intensity of light scattered by fine particles floating in the fluid is detected by a light receiving system to determine the properties of the particles, comprising the steps of calculating the particle diameter from the detected intensity of the scattered light, determining a ratio of light scattering efficiency of the particles in the fluid to the light scattering efficiency of the same particles in a standard fluid on the basis of the refractive index of the fluid in use, and correcting the particle diameter depending upon the ratio of the light scattering efficiency.

In a preferred embodiment, the particle diameter is corrected by correcting a set value for discriminating the particle diameter or by correcting the intensity of the detected scattered light.

Thus in accordance with the invention, the scattering efficiency ratio of the particles is calculated from the refractive index of the fluid used in the measurement and the results of the measurement can then be corrected in accordance with the calculated ratio at the time of calculating the particle properties, particularly the particle diameter. Alternatively, the measurement conditions can be corrected on the basis of the calculated ratio.

BRIEF DESCRIPTION OF THE DRAWINGS

The objects and features of the present invention will become more apparent from the following detailed description taken in conjunction with the accompanying drawings, in which:

FIGS. 2 and 3 are flow charts showing measurement procedures carried out in the apparatus of FIG. 1.

FIG. 5 is a diagram showing a relation between refractive index and scattering efficiency.

DETAILED DESCRIPTION OF THE PREFERRED EMBODIMENTS

Figure 1:
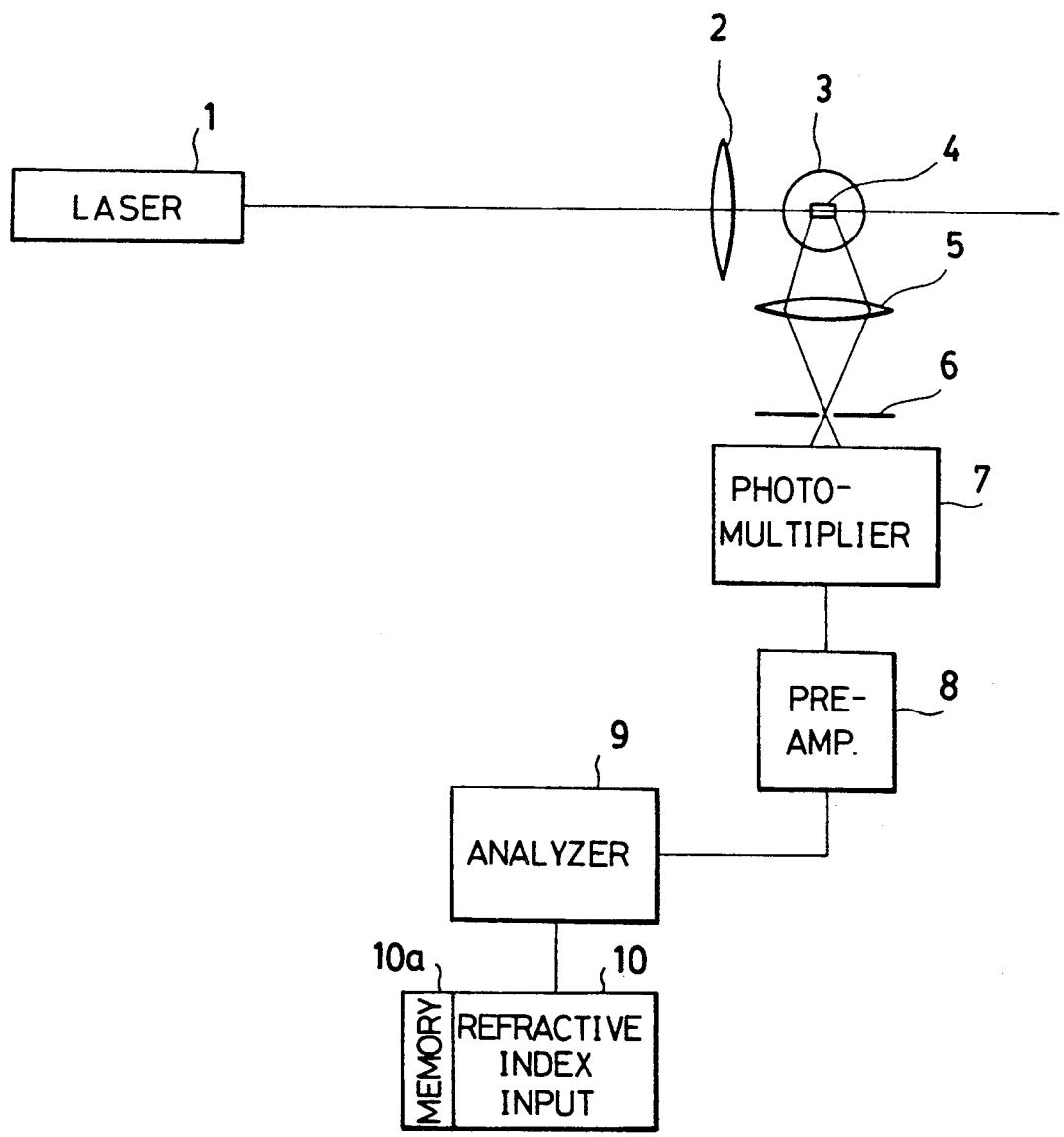
FIG. 1 is a block diagram of a particle measurement apparatus according to the present invention.

The invention will now be explained in detail with reference to the embodiment shown in FIG. 1, which illustrates a particle measurement apparatus employing the present invention. Components of the apparatus of FIG. 1 which are identical with those of the prior art apparatus of FIG. 4 are assigned like reference numerals to those in FIG. 4 and will not be explained in detail again here.

Figure 4:
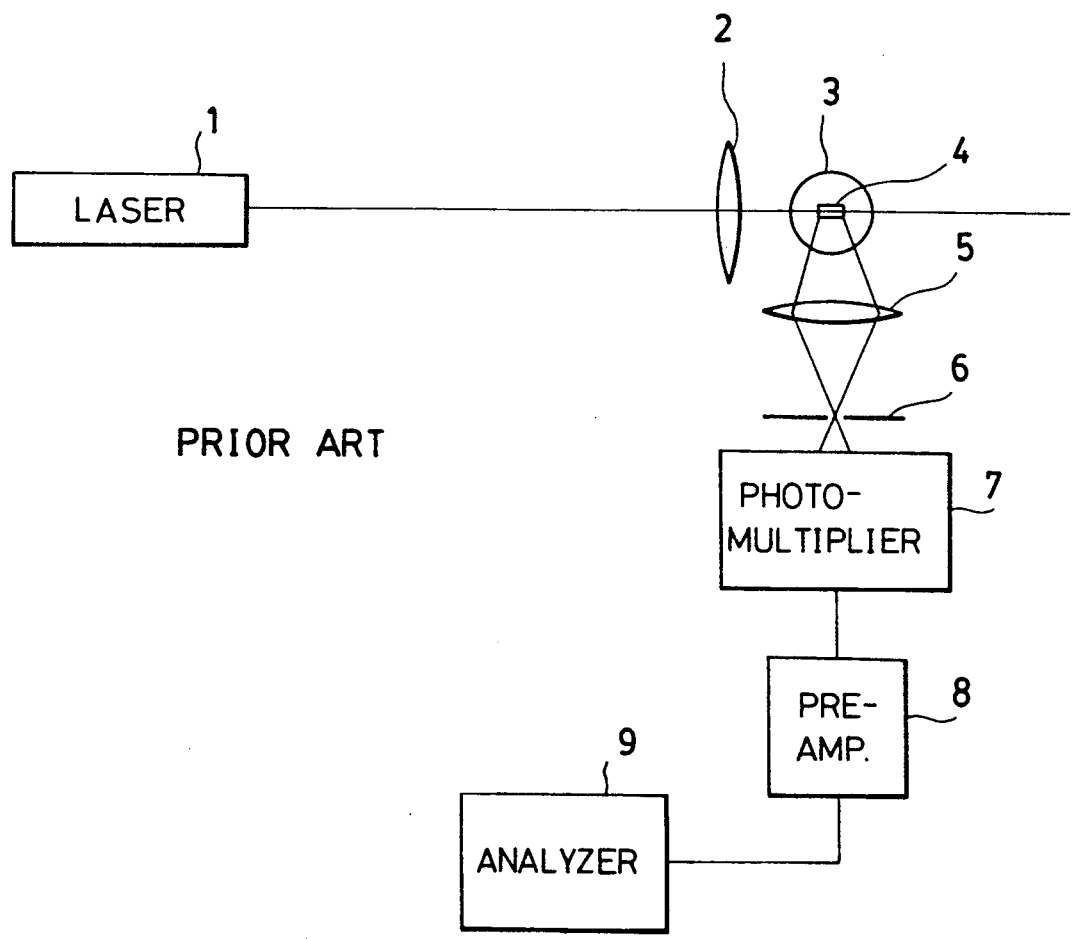
FIG. 4 is a block diagram of a prior art particle measurement apparatus.

A comparison of FIG. 1 and FIG. 4 shows that the arrangement of the apparatus in accordance with this invention is identical with that of the prior art apparatus as regards the portion between the laser beam source 1 and the preamplifier 8, i.e. as regards the system for irradiating the measurement cell 3 and the structure up to the point of converting the light scattered from the particles into an electric signal. However, since in the apparatus according to this embodiment the particle size distribution analysis in the particle size distribution analyzer 9 is controlled in accordance with the refractive index of the fluid in the measurement cell 3, there is further provided a refractive index input device 10 for inputting the refractive index of the fluid in use to the particle size distribution analyzer 9.

The refractive index input device 10 can be constituted as a keyboard or the like through which the operator inputs the refractive index n of the fluid being used as numerical data. Alternatively, a detector (not shown) for automatically measuring the refractive index of the fluid can be provided on the measurement cell 3 and the refractive index input device 10 can be arranged to input the result of the measurement to the particle size distribution analyzer 9 automatically.

The relationship between the refractive index of the fluid and the scattering efficiency of the particles (as shown in FIG. 5) is calculated in advance based on water as a standard and the result is stored in a memory 10a provided in the refractive index input device 10.

Once the refractive index has been input to the apparatus, the ratio of the scattered light intensity to that in the case where the fluid is water is calculated from the aforesaid data using an interpolation method. For this purpose it is possible to use Lagrange interpolation, spline interpolation or the like.

In view of the need to carry out this processing, the refractive index input device 10 is provided with a microprocessor-based processing system or the like.

In evaluating particle properties using the apparatus of the aforesaid arrangement, the refractive index input device 10 is first used for inputting the refractive index of the fluid. The refractive index input device 10 reads out the relationship between the refractive index of the fluid and the scattering efficiency from the memory 10a and calculates the scattering efficiency ratio corresponding to the fluid.

The particle size distribution analyzer 9 then calculates the particle diameter using the so-obtained scattering efficiency ratio. At this time the intensity of the light scattered by the particles is corrected so as to enable a conversion to the particle size distribution in the standard fluid. There are two methods available for carrying out correction based on the refractive index of the fluid when calculating the particle diameter from the intensity of the light scattered from the particles.

One of these methods is shown in FIG. 2. In this method, the measured value of the intensity of the light scattered by the particles is fixed and a set value for discriminating particle diameter is corrected using the scattering efficiency ratio obtained from the refractive index input device 10. In the other method, shown in FIG. 3, the set value for discriminating the particle diameter is fixed and the measured value of the intensity of the light scattered by the particles is itself corrected using the scattering efficiency ratio obtained from the refractive index input device 10.

Consider, for example, the case where 0.2 micrometer particles having a refractive index of 1.592 are present in water (refractive index: 1.333) and the case where the same particles are present in trichloroethylene (refractive index: 1.478). Where the laser beam has a wavelength of 633 nm, the particle light scattering efficiency ratio between the case of water and the case of trichloroethylene is about 1 : 0.192. In other words, the light scattering efficiency of particles present in trichloroethylene is about 1/5.2 that of particles present water.

Thus where only the effect of the refractive index of the fluid on the scattering efficiency of the particles is taken into consideration, the intensity of light scattered from particles present in trichloroethylene can be made equivalent to that of light scattered from the same particles present in water either by using as the set value for discriminating particle diameter in trichloroethylene one that is 1/5.2 times that for discriminating particle diameter in water or by multiplying the intensity of the scattered light from the particles present in the trichloroethylene by about 5.2.

The procedures shown in FIGS. 2 and 3, namely the measurement procedures executed in the particle size distribution analyzer 9 and the refractive index input device 10, will now be explained.

Referring first to FIG. 1, the procedure starts from step S1 in which the refractive index of the fluid being used in the measurement is input from refractive index input device 10. As was mentioned earlier, this is achieved either through a keyboard or a refractive index detector of the refractive index input device 10.

The procedure then advances to step S2 in which the scatter efficiency data corresponding to the fluid is read from the memory 10a, in which the data of FIG. 5 is stored, and then to step S3 in which a scatter efficiency ratio corresponding to the refractive index input to the refractive index input device 10 by the operator (or automatically) is calculated by interpolation. As was explained earlier, this scatter efficiency ratio is the scattered light intensity ratio with respect to the fluid defined as having the standard refractive index (i.e. water).

In the ensuing step S4, the particle size distribution analyzer 9 discriminates the particle diameter from the peak intensity of the scattered light from the particles by a known processing method on the assumption that the refractive index of the liquid is equal to that of water (that the fluid being is used is water) but at this time the set value for discriminating particle diameter is corrected based on the scatter efficiency ratio obtained in step S3. In the case of the aforesaid trichloroethylene, the set value for discriminating particle diameter is set at 1/5.2 times that in the case of water.

In the routine according to FIG. 3, procedures identical to those explained above are conducted in steps S1 to S3 for inputting the refraction ratio and deriving the scatter efficiency ratio corresponding to the input refraction ratio. Then in step S4 the measured value of the intensity of the scattered light is corrected on the assumption that the fluid being used is water. In the case where the fluid is trichloroethylene it suffices to multiply the measured value of the intensity of the scattered light by approximately 5.2 in step S4 of FIG. 3. The so-corrected measured value of the intensity of the scattered light is used for evaluating the particle diameter.

As will be understood from the foregoing, the refractive index of the fluid being used is input by the refractive index input device 10, the scatter efficiency ratio corresponding to the refractive index of the fluid is obtained, and the scatter efficiency ratio is used to correct the measured value of the intensity of the scattered light or the result of the particle diameter evaluation. It is thus possible to ascertain the particle diameter with high accuracy.

While the foregoing explanation of the invention is limited to the aspect of particle diameter evaluation, if such measurement conditions as the velocity of the fluid in the measurement zone, the area of the measurement field and the measurement period are fixed, it further becomes possible to use the results of the particle diameter evaluation obtained through the aforesaid correction processing in the processing for calculating the number and density of the particles from the particle diameter conditions and thus to obtain the number and distribution of the particles within a unit volume of the fluid with high accuracy.

It will be understood that the invention is not limited to the use of trichloroethylene as the fluid but can be applied with like effect to other fluids with different refractive indices. Nor is the invention limited to the use of water as the standard fluid.

As set out above, in the particle measurement method and apparatus according to this invention, a laser beam is directed into a fluid, light scattered by fine particles floating in the fluid is detected by a light receiving system and the properties of the particles are measured from the detected intensity of the scattered light by a process including a step of calculating from the refractive index of the fluid being used the ratio of the light scattering efficiency of the particles being used in the fluid being used to that of the same particles in a standard fluid and a step of correcting the results of the measurement or the measurement conditions in accordance with the calculated ratio. Thus in accordance with the invention, the scattering efficiency ratio of the particles is calculated from the refractive index of the fluid used in the measurement and then, at the time of calculating the particle properties, particularly the particle diameter, either the results of the measurement or the measurement conditions are corrected in accordance with the calculated ratio. The invention thus has the outstanding effect of enabling highly accurate measurement of the particle properties.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A particle measurement method in which a laser beam is directed into a fluid, and the intensity of light scattered by fine particles floating in the fluid is detected by a light receiving system to determine the properties of the particles, comprising the steps of:
   calculating the particle diameter from the detected intensity of the scattered light;
   determining a ratio of the light scattering efficiency of the particles in the fluid which has an index of refraction to the light scattering efficiency of the same particles in a standard fluid having a standard index of refraction; and
   correcting the particle diameter depending upon the ratio of light scattering efficiency.

2. A method as set forth in claim 1, wherein the particle diameter is corrected by correcting a set valve for discriminating the particle diameter from the detected scattered light.

3. A method as set forth in claim 1, wherein the particle diameter is corrected by correcting the value of intensity of the detected scattered light.

4. A particle measurement apparatus in which a laser beam is directed into a fluid, and the intensity of light scattered by fine particles floating in the fluid is detected by a light receiving system to determine the properties of the particles, comprising:
   means for calculating the particle diameter from the detected intensity of the scattered light;
   means for inputting the refractive index of the fluid;
   means for determining a ratio of the light scattering efficiency of the particles in the fluid to the light scattering efficiency of the same particles in a standard fluid having a standard index of refraction; and
   means for correcting the particle diameter depending upon the ratio of light scattering efficiencies by correcting a set value for discriminating the particle diameter from the detected scattered light or by correcting the value of intensity of the detected scattered light.

5. An apparatus as set forth in claim 4, including means for inputting the refractive index of the fluid manually or automatically.

6. A method of measuring the diameter of particles contained in a fluid comprising the steps:
   directing laser light at a fluid containing particles to cause the particles to scatter the laser light;
   determining a scatter efficiency ratio of the light scattering efficiency of the particles in the fluid to the light scattering efficiency of the same particles in a standard fluid based on the refractive indices of the fluid and the standard fluid;
   detecting the intensity of the light scattered by the particles;
   determining the particle diameter using a set value for discriminating the particle diameter from the detected intensity of the scattered light; and
   correcting the particle diameter according to the scatter efficiency ratio.

7. A method according to claim 6; wherein the correcting step comprises correcting the particle diameter by varying the set value depending on the scatter efficiency ratio.

8. A method according to claim 6; wherein the correcting step comprises correcting the particle diameter by varying the intensity of the detected scattered light depending on the scatter efficiency ratio.

9. A method according to claim 6; wherein the step of determining the scatter efficiency ratio includes storing light scattering efficiency data corresponding to different refractive indices in a memory, and reading out from the memory light scattering efficiency data for determining the scatter efficiency ratio.

* * * * *